United States Patent
Takahashi et al.

(10) Patent No.: US 8,214,959 B2
(45) Date of Patent: Jul. 10, 2012

(54) ACTUATOR AND ELECTRIC TOOTHBRUSH USING THE SAME

(75) Inventors: Yuki Takahashi, Tama (JP); Shigenori Inamoto, Tama (JP); Yasutaka Kitamura, Tama (JP)

(73) Assignee: Mitsumi Electric Co., Ltd., Tokyo (JP)

( * ) Notice: Subject to any disclaimer, the term of this patent is extended or adjusted under 35 U.S.C. 154(b) by 692 days.

(21) Appl. No.: 12/318,511

(22) Filed: Dec. 30, 2008

(65) Prior Publication Data

US 2009/0320219 A1 Dec. 31, 2009

(30) Foreign Application Priority Data

Jun. 25, 2008 (JP) ................................. 2008-166535

(51) Int. Cl.
*A46B 13/02* (2006.01)

(52) U.S. Cl. .................. 15/22.1; 15/22.4; 15/23; 15/24; 15/28; 15/105; 15/167.1

(58) Field of Classification Search .................... 15/22.1, 15/22.4, 21.1, 23, 24, 28, 167.1, 105
See application file for complete search history.

(56) References Cited

U.S. PATENT DOCUMENTS

| | | | |
|---|---|---|---|
| 4,736,485 A * | 4/1988 | Egner-Walter et al. | 15/250.202 |
| 5,189,751 A | 3/1993 | Giuliani et al. | |
| 5,721,723 A * | 2/1998 | Uchimaru et al. | 720/669 |
| 2005/0235438 A1 | 10/2005 | Motohashi et al. | |
| 2006/0168745 A1 * | 8/2006 | Kobayashi et al. | 15/22.1 |
| 2007/0040457 A1 | 2/2007 | Shimizu et al. | |

FOREIGN PATENT DOCUMENTS

| | | |
|---|---|---|
| EP | 1 923 985 A1 | 5/2008 |
| JP | 8-65990 A | 3/1996 |
| JP | 9-205763 A | 8/1997 |
| JP | 3243529 | 10/2001 |
| JP | 2002-078310 | 3/2002 |
| JP | 2004-343931 A | 12/2004 |
| JP | 2005-95739 A | 4/2005 |
| JP | 2008-58660 A | 3/2008 |
| WO | WO 92/16160 | 10/1992 |

* cited by examiner

*Primary Examiner* — Robert Scruggs
(74) *Attorney, Agent, or Firm* — Washida & Associates (57) ABSTRACT

An actuator allows miniaturization by realizing back-and-forth rotating motion of, for example, an electric brush without a drive transmitting mechanism which is a separate entity from a drive source. In a movable body (110) of this actuator (100), an outer yoke (150) is provided with sidewalls (152 and 153) located opposing each other spaced a predetermined interval apart. A magnet (160) is provided in the outer yoke (150) through a non-magnetic body (170) and has different magnetic poles located opposing to the opposing inner wall planes of the outer yoke (150) through the air gaps. The movable body (110) is provided with a shaft (180). The fixed body (120) has a coil (128) which is located in the air gaps and which circles the magnet (160). The fixed body (120) movably supports the movable body (110) through elastic bodies (130). An alternating current supplying section (140) supplies to the coil (128) the alternating current of a frequency virtually equal to the resonance frequency of the movable body (110).

5 Claims, 10 Drawing Sheets

ACTUATOR AND ELECTRIC TOOTHBRUSH USING THE SAME

CROSS REFERENCE TO RELATED APPLICATIONS

The disclosure of Japanese Patent Application No. 2008-166535, filed on Jun. 25, 2008, including the specification, drawings and abstract, is incorporated herein by reference in its entirety.

BACKGROUND OF THE INVENTION

1. Field of the Invention

The present invention relates to an actuator used in, for example, an electric toothbrush and electric sonic wave toothbrush.

2. Description of the Related Art

Conventionally, for electric toothbrushes including electric sonic wave toothbrushes, bass brushing toothbrushes that place the brush obliquely (at about forty five degrees) on the boundary part between teeth and gum and vibrate the brush left and right in linear back-and-forth motion, and rolling brushing toothbrushes that move in back-and-forth (backward and forward) rotating motion in a range of a predetermined angle around the shaft and rotating the brush from the gum toward teeth, are known.

For the drive of these toothbrushes, structures are commonly employed for making linear back-and-forth motion or back-and-forth rotating motion for rotation of a rotating DC motor, which makes typical rotation around the shaft, through a motion direction converting mechanism. Further, other than these structures, structures for moving a toothbrush in linear back-and-forth motion by a linear drive actuator or structures for moving a toothbrush in back-and-forth rotating motion by resonating a resonance vibrating mechanism, which constitutes a separate entity from the drive source, by the vibration of the actuator, are known.

As disclosed in Japanese Patent Application Laid-Open No. 2002-078310, the structures for moving a toothbrush in linear back-and-forth motion by a linear drive actuator realize bass brushing by directly producing back-and-forth vibration in the axial direction of an output shaft directly connected with the toothbrush part. According to this structure, there is little power loss due to the motion converting mechanism and furthermore high-speed vibration can be performed.

Further, as disclosed in Japanese Patent No. 3243529, a structure with an actuator and a resonance vibrating mechanism which constitutes a separate entity from the drive source, realizes rolling brushing by exciting the resonance vibrating mechanism with a lever arm by a driving means with electric magnets and permanent magnets and by making the lever arm directly connected coaxially with the toothbrush part move in bobble-head motion.

By the way, there is a demand for an electric toothbrush that realizes rolling brushing, and there is also a demand for miniaturization of the drive part of the toothbrush because making slimmer a handle part in which the drive part and driving the rolling brushing toothbrush is demanded.

However, to realize rolling brushing using a motor that makes typical rotation around the shaft, a motion direction converting mechanism for converting the rotation of the motor into back-and-forth rotating motion, is required in addition to the motor. Further, to realize rolling brushing using a linear drive actuator as shown in Japanese Patent Application Laid-Open No. 2002-078310, a torque generating mechanism (i.e. drive source) is required in addition to the linear drive actuator.

Further, the structure disclosed in Japanese Patent No. 3243529 requires a drive source and a resonance vibrating mechanism apart from the drive source.

In this way, to use a motor or linear drive actuator for the drive source of an electric toothbrush, conventional structures need to secure spaces for locating the drive source and, in addition, the motion direction converting mechanism, torque generating mechanism or resonance vibrating mechanism, apart from the drive source and therefore there is a problem that miniaturization of a toothbrush is difficult.

Further, if a drive transmitting mechanism such as a motion direction converting mechanism which constitutes a separate entity from an actuator such as a motor is provided in the drive part of the toothbrush, there are concerns that, in the drive transmitting mechanism, noise is generated and efficiency deteriorates due to occurrence of loss in transmitted power, and therefore countermeasures for these need to be taken into account.

SUMMARY OF THE INVENTION

It is therefore an object of the present invention to provide a small actuator and electric toothbrush that realizes back-and-forth rotating motion of, for example, an electric toothbrush without a drive transmitting mechanism which constitutes a separate entity from the drive source.

The present invention achieves the above object by employing a configuration including: a movable body that has: an outer yoke having opposing inner wall planes spaced a predetermined interval apart; and a magnet which is provided in the outer yoke and in which different magnetic pole planes oppose the opposing inner wall planes through air gaps; an output shaft provided in the movable body; a fixed body that has a coil which is located in the air gaps and which encircles the magnetic body; an elastic support part that movably supports the movable body in the fixed body; and an alternating current supplying section that supplies to the coil an alternating current of a frequency substantially equal to a resonance frequency of the movable body.

Further, the present invention achieves the above object by employing a configuration including: an actuator having the above configuration; and a toothbrush part that is coupled to an output shaft of the actuator on the same shaft center as the output shaft and that has in a head part a hair bundle part provided orthogonal to an axial direction.

DETAILED DESCRIPTION OF THE PREFERRED EMBODIMENT

Hereinafter, embodiments of the present invention will be described in detail with reference to the accompanying drawings.

Embodiment 1

Figure 1:
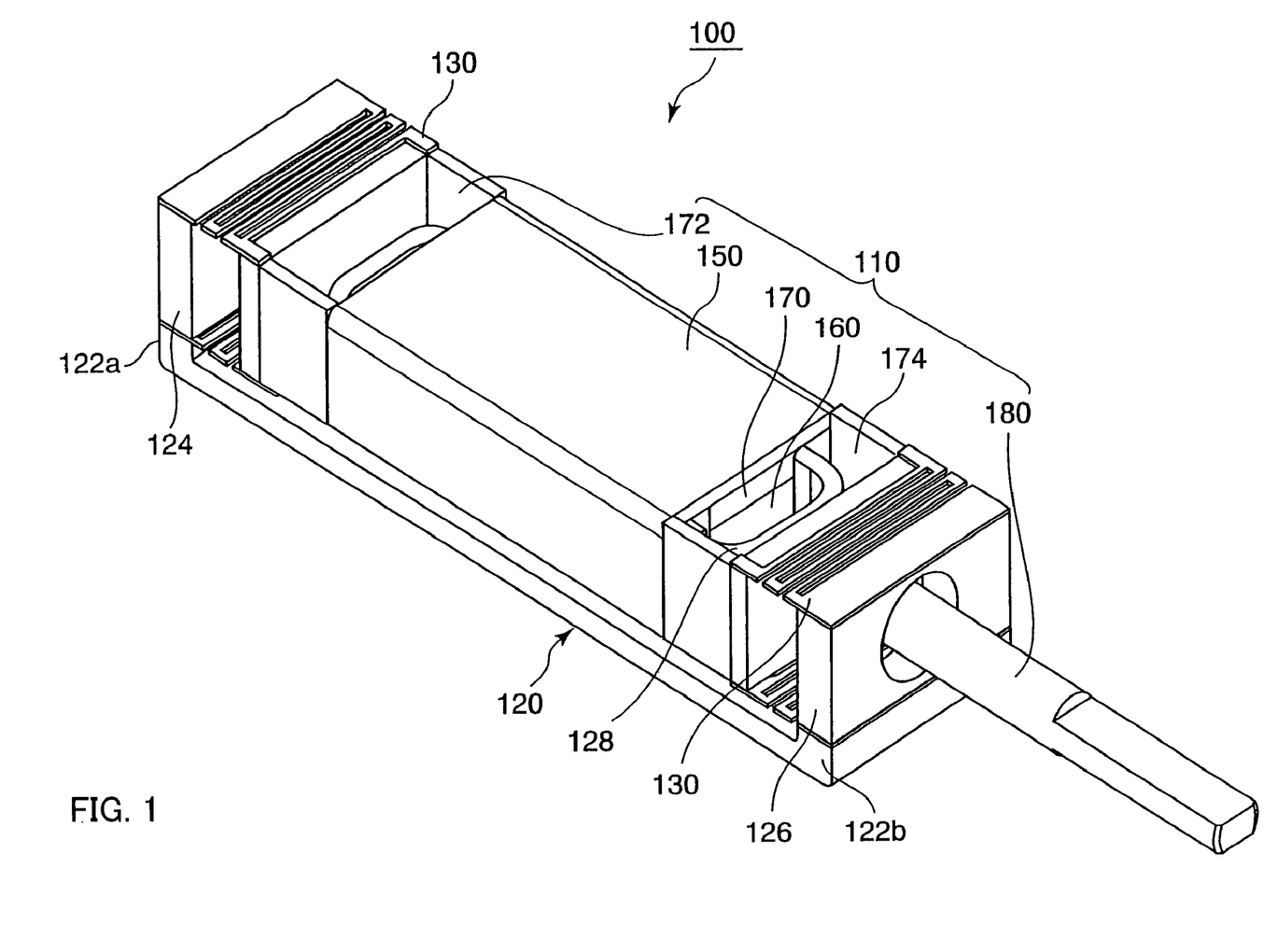
FIG. 1 is a perspective view showing an actuator according to Embodiment 1 of the present invention.
Figure 2:
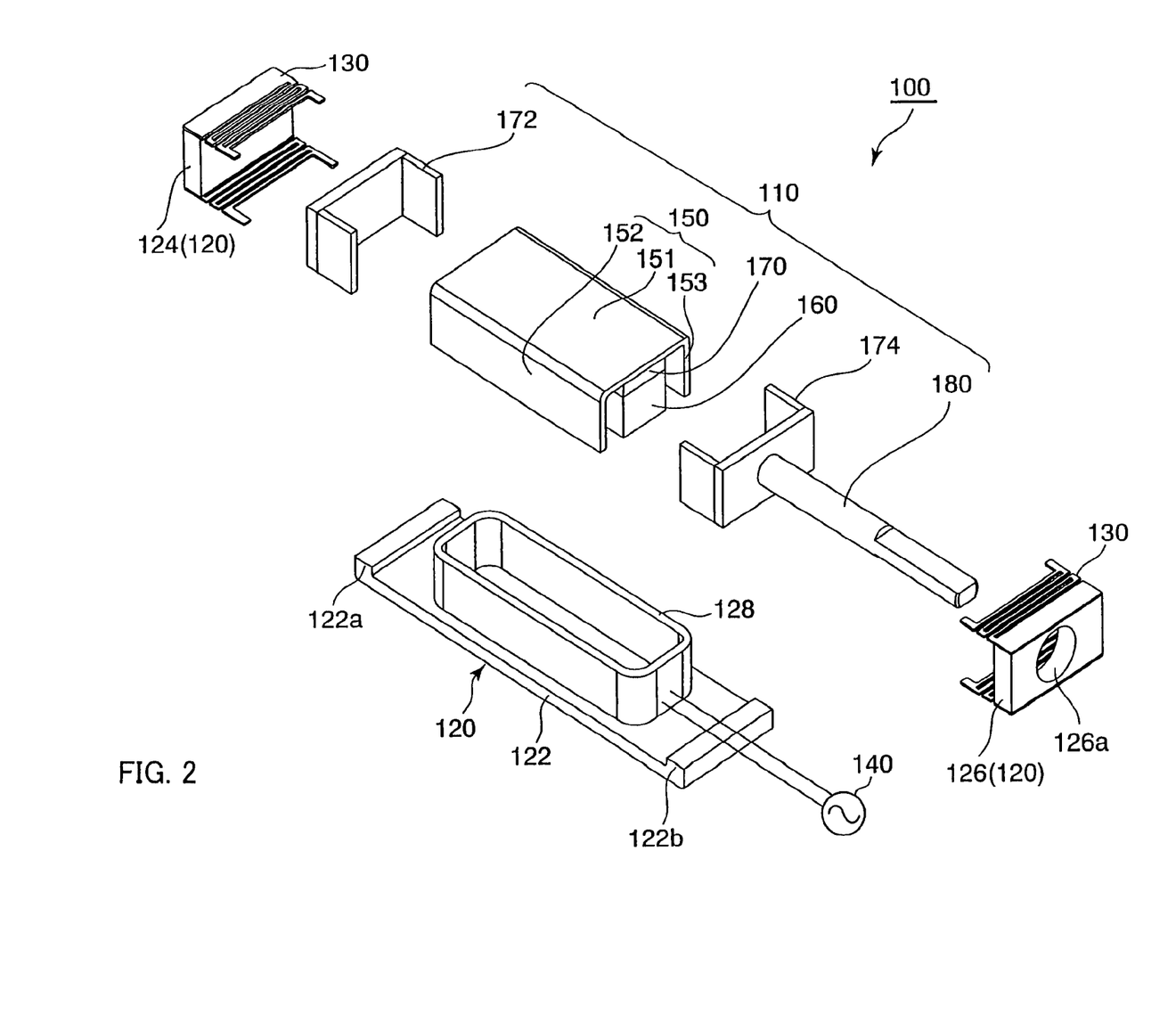
FIG. 2 is an exploded perspective view showing main parts of the actuator.
Figure 3:
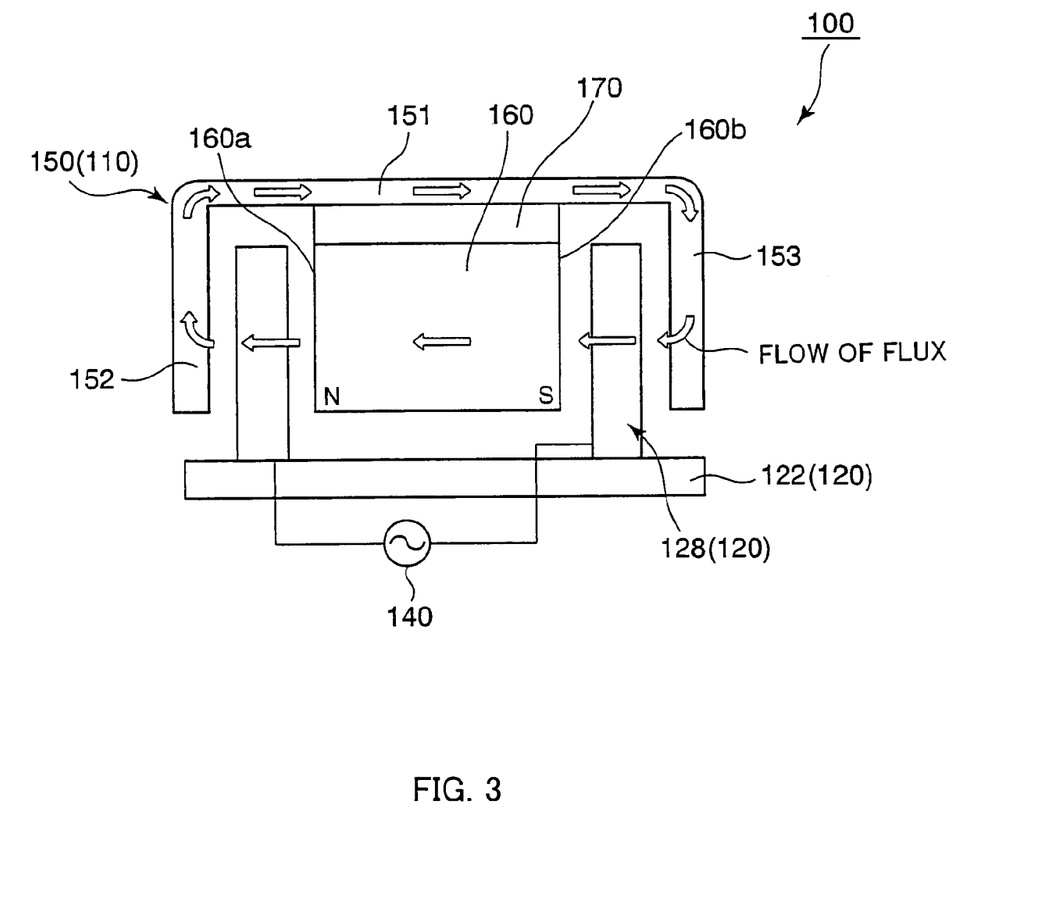
FIG. 3 is a schematic cross-sectional view showing configurations of a movable body and fixed body in the actuator.

FIG. 1 is a perspective view showing actuator 100 according to Embodiment 1 of the present invention. FIG. 2 is an exploded perspective view showing main parts of the actuator. FIG. 3 is a schematic cross-sectional view showing configurations of a movable body and fixed body in actuator 100.

As shown in FIG. 1, actuator 100 has movable body 110, fixing body 120, elastic bodies 130 that movably support movable body 110 in fixed body 120, and alternating current supplying section 140 (FIG. 2 and FIG. 3).

Movable body 110 has outer yoke 150, magnets 160, elastic body connecting parts 172 and 174 and back-and-forth rotating vibration transmission shaft (hereinafter "shaft") 180 provided in movable body 110.

Fixed body 120 has base 122, support walls 124 and 126 and coil 128 (see FIG. 2). In fixed body 120, coil 128 is located in the center part of the surface of base 122 which has a long rectangular plate shape extending in the direction in which shaft 180 extends. Further, support walls 124 and 126 are provided upright from side edges spaced apart in the longitudinal direction of base 182. Furthermore, as shown in FIG. 2, alternating current power is supplied from alternating current supplying section 140 to coil 128.

As shown in FIG. 2 and FIG. 3, outer yoke 150 forms a virtually U-shaped cross section and is formed by bending a flat magnetic body. Outer yoke 150 has rectangular flat yoke center part 151 and sidewalls 152 and 153 that drop from both side edges of yoke center part 151 and that oppose each other.

Outer yoke 150 is attached with elastic body connecting parts 172 and 174 connected with support walls 124 and 126 through elastic bodies 130, in the ends (i.e. ends spaced apart in the direction in which both side edges extend) spaced apart in the longitudinal direction of outer yoke 150 (corresponding to the direction in which shaft 150 extends).

One of elastic body connecting parts 172 and 174 is attached with shaft 180 projecting in the same direction as the direction in which outer yoke 150 extends. That is, shaft 180 is provided projecting from elastic body connecting part 174 attached to outer yoke 150, in a virtually orthogonal direction with respect to the direction in which magnet 160 opposes sidewalls 152 and 153. Further, elastic body connecting parts 172 and 174 are preferably made non-magnetic bodies.

In this way, shaft 180 is fixed to outer yoke 150 through elastic body connecting part 174 such that shaft 180 is attached to movable body 110 so as to be located on the shaft line running on the center of gravity of movable body 110. Shaft 180 thereby produces back-and-forth rotating vibration with movable body 110 and transmits the vibration to the outside.

Further, when actuator 100 is used in an electric toothbrush, shaft 180 is coupled with the toothbrush part having in the head part a hair bundle part provided on the same shaft center as shaft 180 and provided orthogonal to the axial direction. By this means, the toothbrush part performs the same motion as shaft 180, that is, rolling, which refers to back-and-forth rotating vibration.

As shown in FIG. 3, magnet 160 is attached through non-magnetic body 170 in the center part in the back of yoke center part 151 of outer yoke 150 such that air gaps are formed between opposing sidewalls 152 and 153 of outer yoke 150. Further, magnet 160 may be provided in outer yoke 150 such that the air gaps are formed between opposing sidewalls 152 and 153 of outer yoke 150 without non-magnetic body 170.

Magnet 160 is provided so as to drop from yoke center part 151 and magnetic poles different from each other are made oppose to the inner wall planes of sidewalls 152 and 153.

Here, the N pole side of magnet 160 opposes the inner wall plane of sidewall 152 of outer yoke 150 and the S pole side opposes the inner wall plane of sidewall 153 of outer yoke 150.

Further, magnet 160 is a rectangular parallelepiped with the length matching the length in the direction in which outer yoke 150 extends, and is attached to yoke center part 151 through non-magnetic body 170 of the same external shape as magnet 160, along the direction in which yoke center part 151 extends.

By this means, magnet 160 has the same length as the length in the longitudinal direction of outer yoke 150, and makes planes of different magnetic poles oppose the entire inner wall planes of opposing sidewalls 152 and 153.

In the air gaps between magnet 160 and sidewalls 152 and 153 of outer yoke 150, coil 128 that is spaced apart from both lateral wall planes (i.e. magnetic planes) 160a and 160b of magnet 160, the inner wall planes of sidewalls 152 and 153 and the back of yoke center part 151 and that circles magnet 160, is located.

Coil 128 is a voice coil and is wound to surround the periphery of magnet 160. To be more specific, in the air gaps, coil 128 is wound in the direction orthogonal to the direction in which magnet 160 opposes sidewalls 152 and 153.

As shown in FIG. 1 and FIG. 2, support walls 124 and 126, provided upright on base 122 on which this coil 128 is provided, are provided on limbs 122a and 122b rising from both side edges spaced apart in the longitudinal direction of base 122. Support wall 126 has opening part 126a through which shaft 150 of movable body 160 is inserted.

By inserting shaft 180 through opening part 126a in this support wall 126, support walls 124 and 126 hold movable body 110 in the virtually horizontal direction in the normal state (virtually parallel to base 122) through elastic bodies 130 bridging between support walls 124 and 126 and elastic body connecting parts 172 and 174.

Elastic bodies 130 displacably support movable body 110 in the left, right, front and back directions in the area where support walls 124 and 126 oppose each other and supports movable body 110 in the twisting direction of magnet 160 and shaft 180. Here, elastic bodies 130 are formed with flat, zig-zag springs provided in the upper and lower ends of opposing planes between support walls 124 and 126 so as to project virtually horizontally in the opposing direction. That is, elastic bodies 130 are provided in a zig-zag arrangement such that a metal plate of a strip shape running from one end toward the other end repeats extending in one width direction and then turning back in the other width direction, and elastic bodies 130 themselves extend and contract in the twisting direction once the one end and the other end are fixed.

Through elastic bodies 130 configured in this way, movable body 110 is movably supported in the twisting direction by support walls 124 and 126 of fixed body 120 in the upper and lower edges of the ends orthogonal to the side edges.

When the inertia of movable body 110 is J and the spring constant in the twisting direction is $k_{sp}$, movable body 110 vibrates on fixed body 120 at the resonance frequency calculated by following equation 1.

(Equation 1)

$$f_0 = \frac{1}{2\pi}\sqrt{\frac{K_{sp}}{J}} \quad [1]$$

In actuator 100 of the present embodiment, alternating current supplying section 140 supplies to coil 128 an alternating current at a frequency virtually equal to resonance frequency $f_0$ of movable body 110. By this means, movable body 110 can be driven efficiently.

In movable body 110 and fixed body 120, outer yoke 150, magnets 160 and coil 128 form a magnetic circuit.

As shown in FIG. 3, in actuator 100, a magnetic circuit is formed such that the fluxes (represented by outline arrows) generated from magnet 160 pass sequentially the air gap in which coil 128 is located, sidewall 152 of outer yoke 150, yoke center part 151, sidewall 153 and the air gap on the opposite side.

Next, the operation of actuator 100 will be described.

Movable body 110 in this actuator 100 adopts a spring mass type structure supported by fixed body 120 through elastic bodies 130, and, when an alternating current of a frequency equal to resonance frequency $f_0$ of movable body 110 is supplied to coil 128, movable body 110 is driven in a resonated state. The back-and-forth rotating vibration produced then is transmitted to shaft 180 of movable body 110.

Actuator 100 is driven based on the motion equation represented by following equation 2 and the circuit equation represented by following equation 3.

(Equation 2)

$$J\frac{d^2\theta(t)}{dt^2} = K_t i(t) - K_{sp}\theta(t) - D\frac{d\theta(t)}{dt} - T_{Load} \quad [2]$$

J: inertia moment [Kgm2]
θ(t) : angle [rad]
$K_t$: torque constant [Nm/A]
i(t): current [A]
$K_{sp}$: spring constant [Nm/rad]
D: attenuation coefficient [Nm/(rad/s)]
$T_{Load}$: load torque [Nm]

(Equation 3)

$$e(t) = Ri(t) + L\frac{di(t)}{dt} + K_e\frac{d\theta(t)}{dt} \quad [3]$$

e(t): voltage [V]
R: resistance [O]
L: inductance [H]
$K_e$: back electromotive force multiplier [V/(rad/s)]

That is, the inertia moment, rotation angle, torque constant, current, spring constant, attenuation coefficient and load torque can be changed appropriately within the range where equation 2 is met, and the voltage, resistance, inductance and back electromotive force multiplier can be changed appropriately within the range where equation 3 is met.

FIG. 4 is a schematic view for illustrating the operation of the actuator according to Embodiment 1. Further, although the outline arrows represent the flow of fluxes in a magnetic circuit by the magnet in FIG. 4A, the flow is the same in FIG. 4B to FIG. 4D and illustration thereof will be omitted.

When the alternating current is supplied to coil 128 from alternating current supplying section 140, thrusts represented by arrows F1, F2, F3 and F4 in FIG. 4, are generated in coil 128 according to Fleming's left hand rule. By this means, in base 122 with coil 128 and movable body 110 attached to support walls 124 and 126 through elastic bodies 130, a torque where the center of gravity of rotation is the shaft center is generated.

The operation of actuator 100 in one cycle will be described.

Figure 4A:
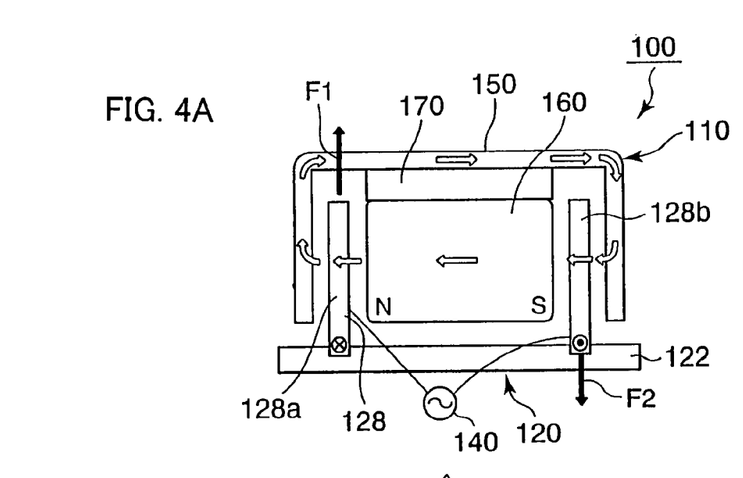
FIG. 4 is a schematic view illustrating the operation of the actuator.

When a current flows into coil 128 in the direction shown in FIG. 4A (this direction is referred to as "the forward current"), upward thrust F1 (in the direction toward outer yoke 150) is generated in part 128a of coil 128 opposing the N pole plane 160a of magnet 160, and downward thrust F2 (in the direction toward base 122) is generated in part 128b of coil 128 opposing the S pole plane 160b of magnet 160.

Figure 4B:
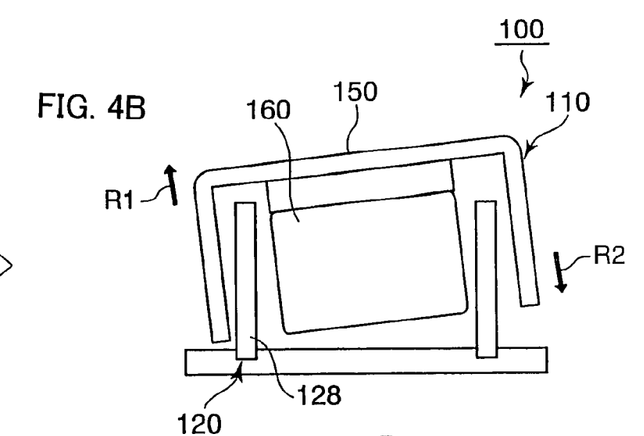

By this means, the opposing rotating force is generated in movable body 110 supported through elastic bodies 130 by support walls 124 and 126 rising from base 122 with coil 128 (see FIG. 1 and FIG. 2), so that movable body 110 can be moved to the location shown in FIG. 4B.

In actuator 100 in the state shown in FIG. 4B, reaction forces represented by arrows R1 and R2 are generated from the restoring forces of elastic bodies 130. From the state shown in FIG. 4B to the state shown in FIG. 4D, the current of the opposite direction to FIG. 4A is supplied to coil 128. By this means, from the state of FIG. 4B to the state of FIG. 4C, movable body 110 rotates clockwise with respect to fixed body 120 by the reaction forces represented by arrows R1 and R2 and the thrusts represented by arrows F3 and F4. Further, from the state of FIG. 4C to the state of FIG. 4D, movable body 110 rotates clockwise with respect to fixed body 120 by the thrusts represented by arrows F3 and F4.

Figure 4C:
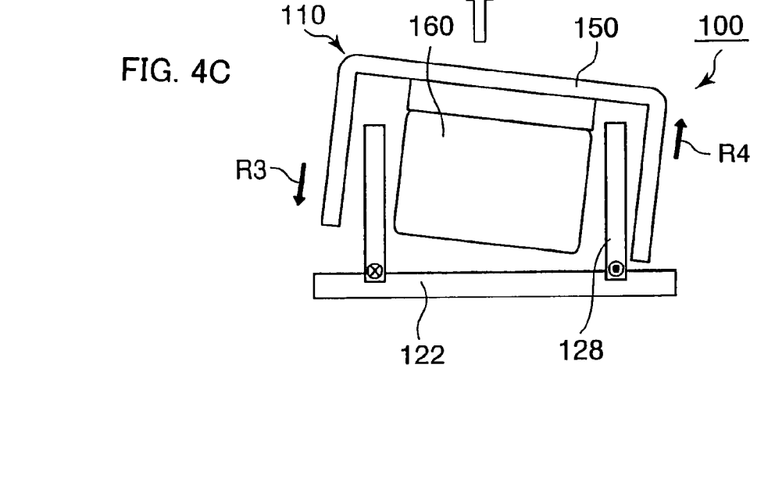
Figure 4D:
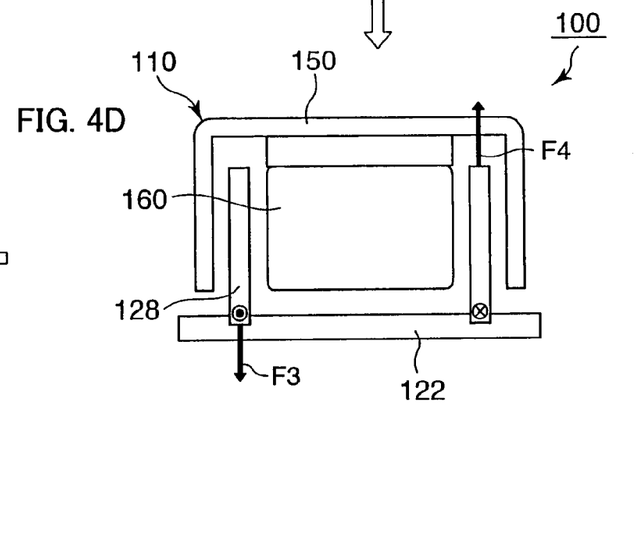

In actuator 100 in the state shown in FIG. 4D, the reaction forces represented by arrows R3 and R4 are generated from the restoring forces of elastic bodies 130. From the state shown in FIG. 4D through the state shown in FIG. 4A to the state shown in FIG. 4B, the forward current is supplied to coil 128. By this means, from the state of FIG. 4D to the state of FIG. 4A, movable body 110 rotates counterclockwise with respect to fixed body 120 by the reaction forces represented by arrows R3 and R4 and the thrusts represented by arrows F1 and F2. Further, from the state of FIG. 4A to the state of FIG. 4B, movable body 110 rotates counterclockwise with respect to fixed body 120 by the thrusts represented by arrows F1 and F2.

Next, the alternating current supplied in each state of FIG. 4 will be briefly described.

Figures 5A, 5B:
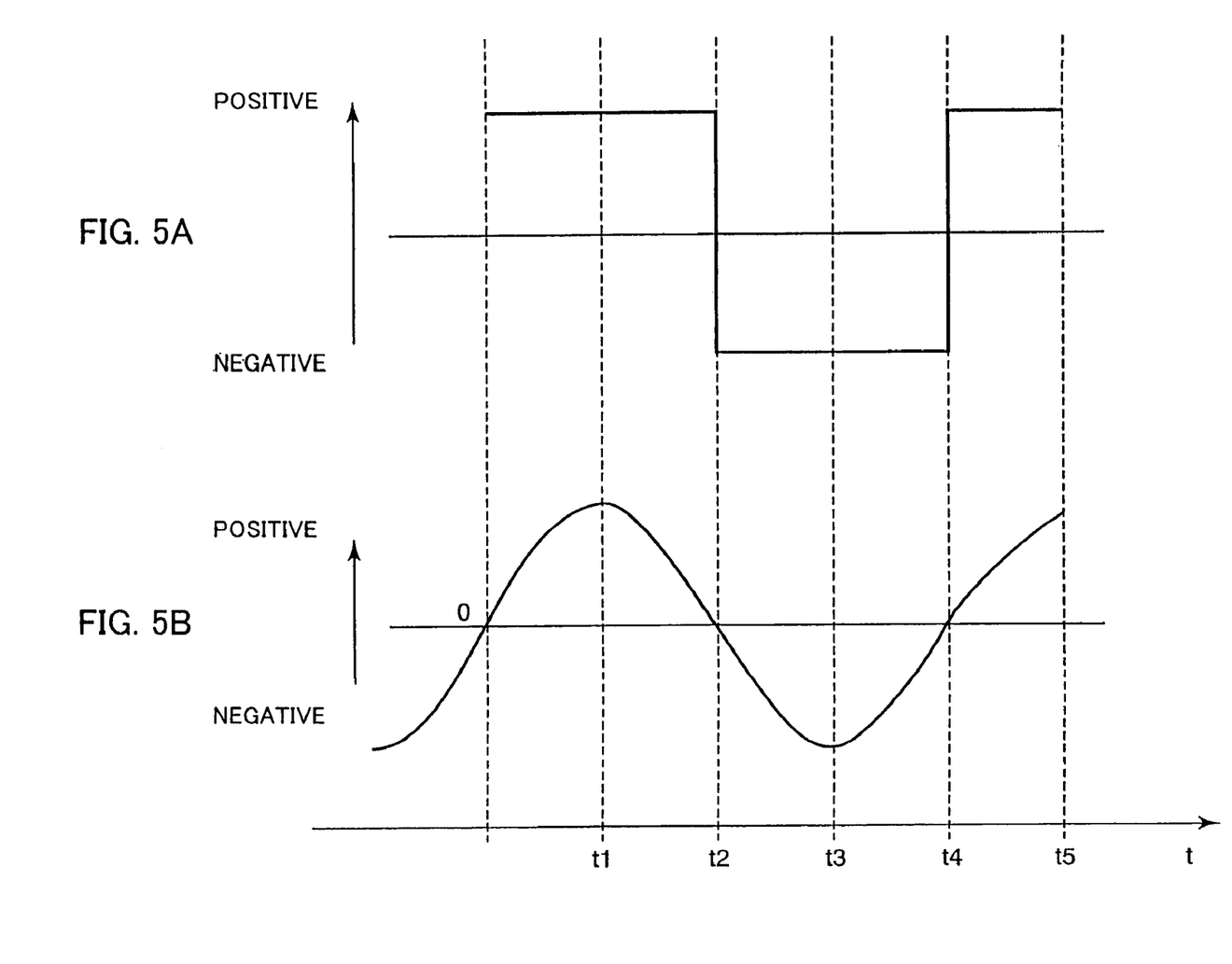
FIG. 5 shows the cycle of the alternating current supplied to a coil in an outer yoke.

The alternating current flowing into the coil may be a pulse wave of frequency $f_0$ as shown in FIG. 5A or a sine wave of frequency $f_0$ as shown in FIG. 5B.

In the state of FIG. 4A, the forward current in time point t1 shown in FIG. 5 is supplied, in the state of FIG. 4B, the direction of the current is switched as shown in time point t2 of FIG. 5 and, in the state of FIG. 4C, the backward current in time point t3 shown in FIG. 5 is supplied. Further, in the state of FIG. 4D, the direction of the current is switched as shown in time point t4 of FIG. 5 and, in the state of FIG. 4D, the forward current in time point t5 shown in FIG. 5 is supplied.

This is the operation in one cycle, and, by repeating such an operation, movable body 110 moves in back-and-forth rotating motion.

In actuator 100, movable body 110 moves in back-and-forth rotating motion, that is, produces back-and-forth rotating vibration, and this back-and-forth rotating vibration is outputted to the outside through shaft 180. When a toothbrush part having in the head part a hair bundle part provided orthogonal to the axial direction is coupled to shaft 180, the toothbrush part produces back-and-forth rotating vibration and enables rolling brushing.

In this way, actuator 100 is driven by the resonance phenomenon in which equations 2 and 3 are met and the resonance frequency represented by equation 1 is used. By this means, in actuator 100, only power consumed in the static state is the loss due to load torque and the loss due to friction, so that driving at low power consumption, that is, back-and-forth rotating vibration of movable body 110 at low power consumption, is possible. As described above, actuator 100 according to the present embodiment allows miniaturization by realizing back-and-forth rotating motion of, for example, an electric toothbrush without a drive transmitting mechanism which constitutes a separate entity from the drive source, and further realizes back-and-forth rotating motion at low power consumption.

Further, in actuator 100, magnet 160 has different magnetic pole planes provided between sidewalls 152 and 153 with respect to outer yoke 150 so as to oppose sidewalls 152 and 153 and is located in side coil 128, thereby forming a magnetic circuit. Compared to a case where a plurality of magnets are attached to the inner wall planes of sidewalls 152 and 153, when the magnetic circuit of the present embodiment is formed, it is possible to decrease the number of magnets, improve the assembly design and reduce the cost. Further, it is possible to provide the above same advantage with an electric toothbrush having actuator 100, and make the electronic toothbrush itself smaller.

Embodiment 2

Figure 6:
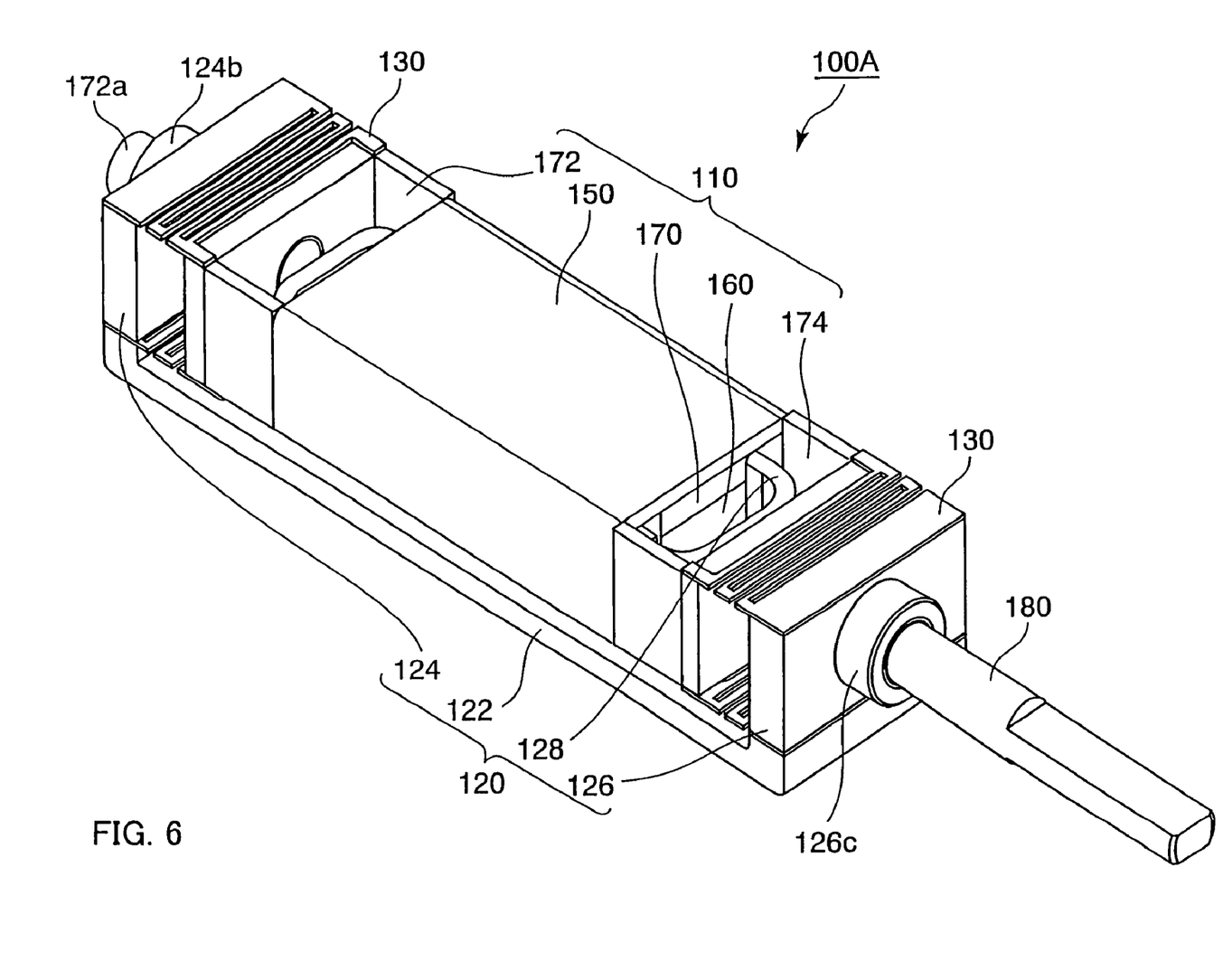
FIG. 6 is a perspective view showing the actuator according to Embodiment 2 of the present invention.
Figure 7:
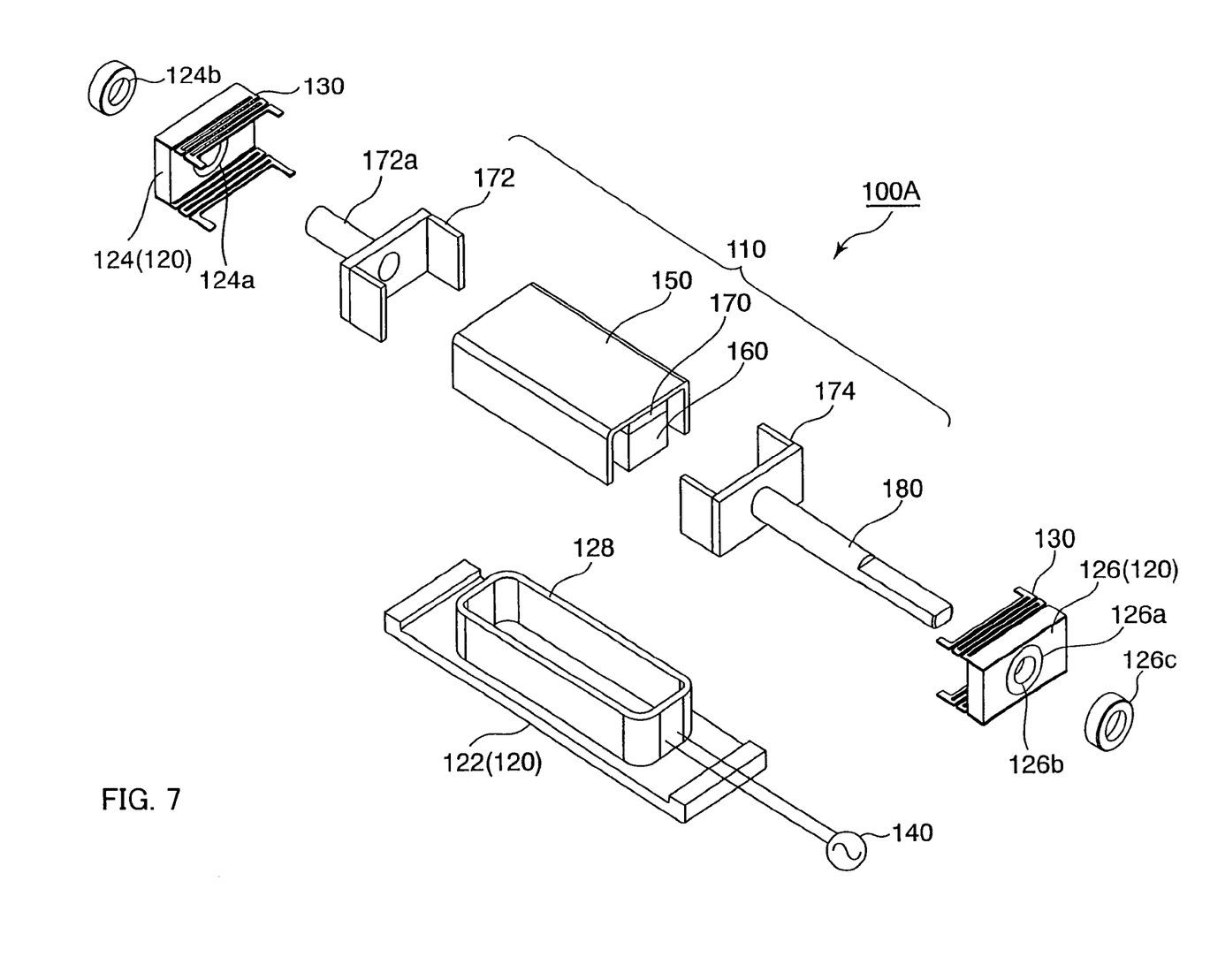
FIG. 7 is an exploded perspective view of the actuator.

FIG. 6 is a perspective view showing the actuator according to Embodiment 2 of the present invention, and FIG. 7 is an exploded perspective view of the actuator. Further, this actuator 100A has the same basic configuration as corresponding actuator 100 in Embodiment 1 shown in FIG. 1, and the same components will be assigned the same reference numerals and description thereof will be omitted.

Actuator 100A employs a configuration where, in actuator 100, movable body 110 is rotatably and axially supported in fixed body 120. Here, in the configuration of actuator 100, movable body 110 is rotatably and axially supported on the same shaft center as shaft 180.

That is, in actuator 100A, bearing 126b is attached to opening part 126a of support wall 126 through which shaft 180 is inserted, in the configuration of actuator 100. Support wall 126 rotatably supports shaft 180 through bearing 126b. Further, bush 126c fits onto the part of shaft 180 projecting from support wall 126.

Furthermore, in elastic body connecting part 172 attached to outer yoke 150, support shaft part 172a located on the same shaft center as shaft 180 is provided projecting in the direction opposite to the direction in which shaft 180 projects. Support shaft part 172a has virtually the same external diameter as the shaft.

Bearing 124a, through which support shaft part 172a is inserted, is attached to support wall 124 connected with this elastic body connecting part 172 through elastic bodies 130. Bush 124b fits onto the end of support shaft part 172a inserted through bearing 124a of support wall 124, in the back of support wall 124.

In this way, in actuator 100A, movable body 110 is rotatably and axially supported by support walls 124 and 126 by means of support shaft part 172a and shaft 180. Therefore, in actuator 100A, an alternating current is supplied to coil 128 from alternating current supplying section 140 and back-and-forth rotating vibration is stably produced around the shaft center of shaft 180 with respect to fixed body 120.

Consequently, it is possible to provide the degree of freedom only in rotation and the axial direction, improve shock robustness of actuator 100 itself and stably allows back-and-forth rotating vibration of movable body 110.

Further, in actuator 10A, shaft 180 that transmits and outputs the movable motion of movable body 110 is used as the shaft part to axially support movable body 110 in fixed body 120.

Embodiment 3

Figure 8:
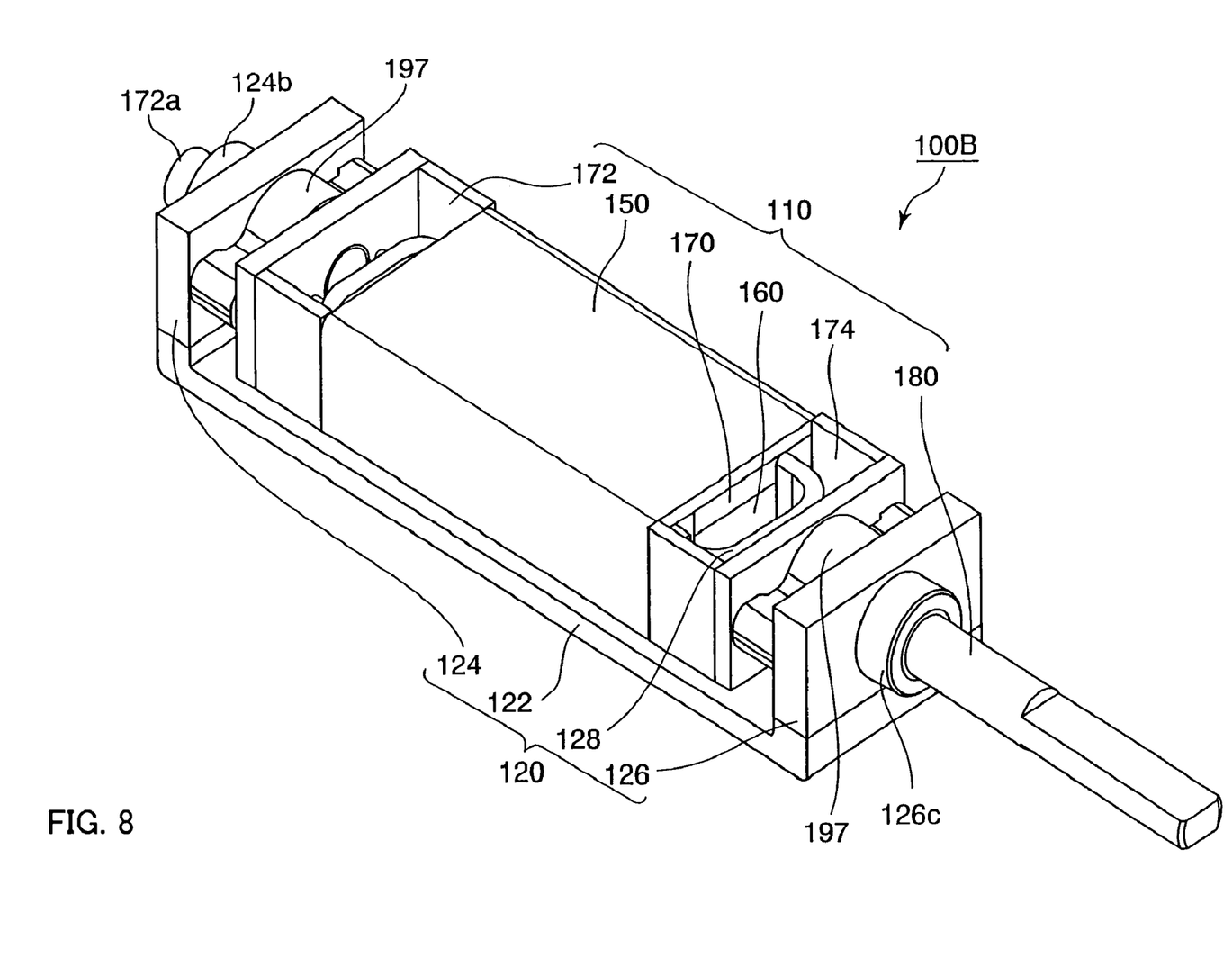
FIG. 8 is a perspective view showing the actuator according to Embodiment 3 of the present invention.
Figure 9:
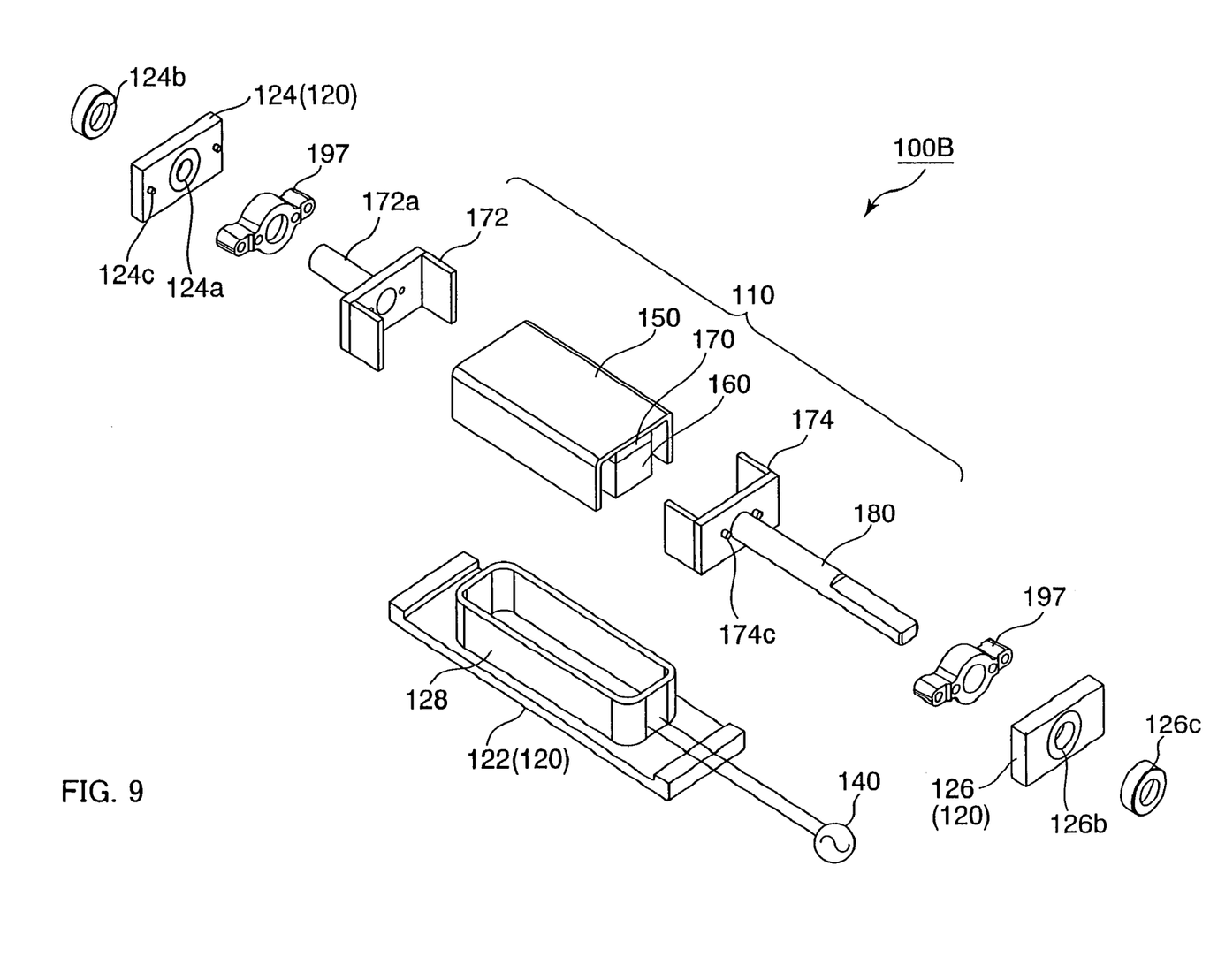
FIG. 9 is an exploded perspective view of the decomposed actuator.
Figure 10:
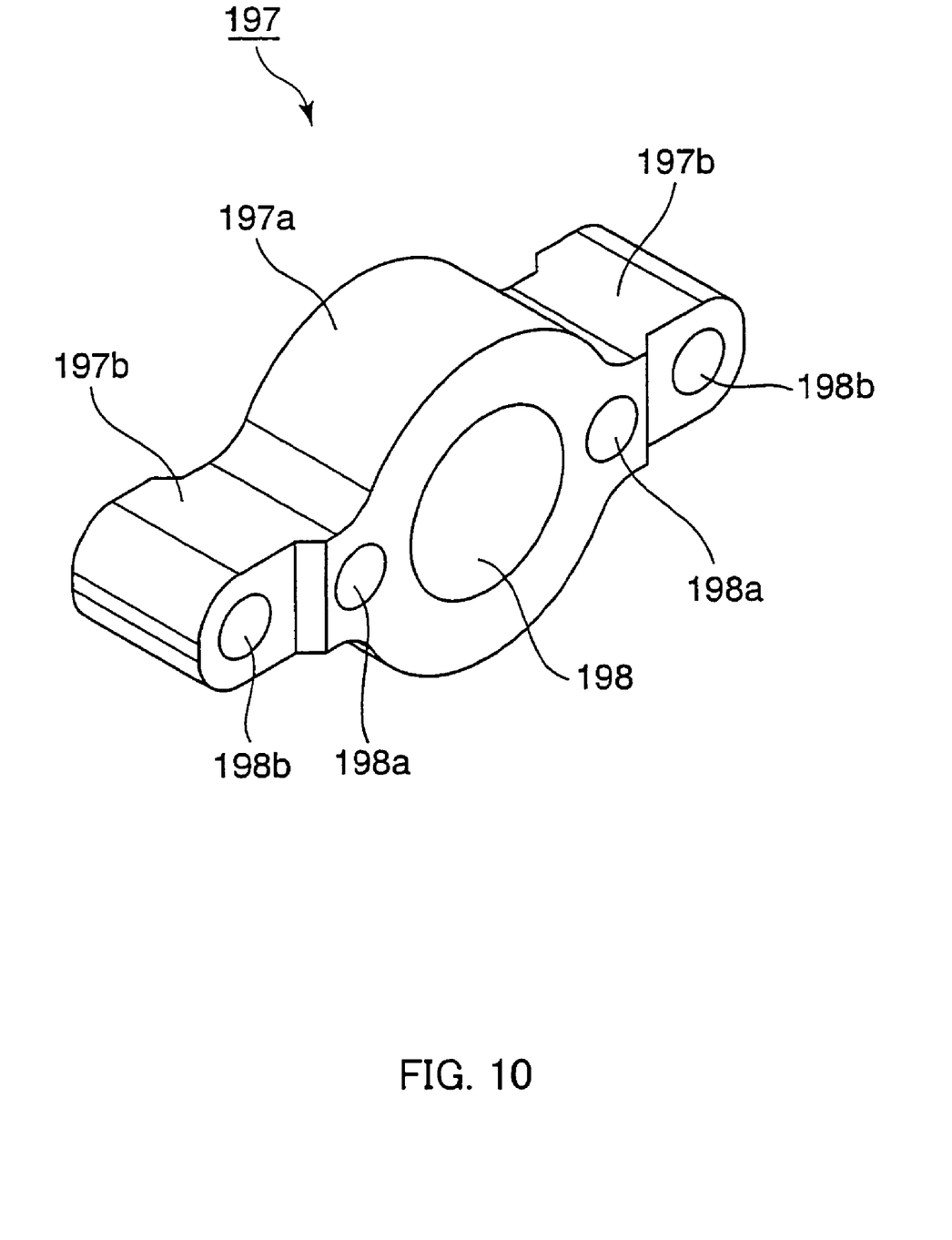
FIG. 10 shows an elastomer which is a viscoelastic body used in the actuator.

FIG. 8 is a perspective view showing the actuator according to Embodiment 3 of the present invention, FIG. 9 is an exploded perspective view of the actuator, and FIG. 10 shows an elastomer which is a viscoelastic body used in the actuator. Further, actuator 100B shown in FIG. 8 and FIG. 9 adopts a structure in which elastic bodies 130 are changed in corresponding actuator 100A in Embodiment 2 shown in FIG. 6 and FIG. 7, and other configurations are the same. Therefore, the same components will be assigned the same reference numerals and description thereof will be omitted.

In actuator 100B, elastomers 197 that are viscoelastic bodies, in which the degree of attenuation is significant, are used in the configuration of actuator 100A instead of elastic bodies 130 which are the same zig-zag springs as elastic bodies 130 of actuator 100 of Embodiment 1.

As shown in FIG. 10, elastomer 197 has center part 197a with inserting through-hole 198 through which support shaft part 172a and shaft 180 are inserted and arm parts 197b projecting from center part 197a in the direction orthogonal to the shaft center of support shaft part 172a and shaft 180.

Elastomer 197 is located between support wall 124 (126) and elastic body connecting part 172 (174) and functions as a spring. In elastomer 197, projections of support wall 124 (126) and elastic body connecting part 172 (174) fit in holes 198a and 198b formed in locations drifted in the direction in which arm parts 197b extend. Further, in FIG. 9, in the projections fitted in holes 198a and 198b of elastomers 197, only projections 124c formed in support wall 124 and projections 174c formed in elastic body connecting part 174, are shown. Although not shown, the same projections as projections 124c of support wall 124 are formed in support wall 126 and the same projections as projections 174c of elastic body connecting part 174 are formed in elastic body connecting part 172. Here, in arm parts 197b of elastomer 197, projections 174c of elastic body connecting part 174 (172) are pressed to fit in holes 198a located close to center part 197a. Further, projections 124c of support wall 124 (126) are pressed to fit in holes 198b located far from center part 197a.

Actuator 100B is able to provide the same advantage as in Embodiment 2, and elastomer 197 can be attached to support wall 124 (126) and elastic body connecting part 172 (174) by arranging elastomer 197 between support wall 124 (126) and elastic body connecting part 172 (174) and pressing against projections (only 124c and 174c are shown in FIG. 9) of support wall 124 (126) and elastic body connecting part 172 (174) to fit in holes 198a and 198b. By this means, unlike a case where a metal spring such as a zig-zag spring is used, troublesome attachment processes such as screwing with screws or bonding are not required, so that the assembly design of actuator 100B itself can be improved.

Further, outer yoke 150 in the above embodiments has inner wall planes opposing different magnetic poles of magnet 160. Outer yoke 150 may be configured in any way as long as outer yoke 150, coil 128 and magnet 160 form a magnetic circuit. Therefore, the entirety of outer yoke 150 may be shaped in an arc-shaped cross section or the yoke body part may be formed in an arc shape.

Further, the above present invention can be variously modified without departing from the spirit of the present invention, and it naturally follows that the present invention embraces the modifications.

The actuator according to the present invention produces advantages of allowing miniaturization by realizing back-and-forth rotating motion of, for example, an electric toothbrush without a drive transmitting mechanism which constitutes a separate entity from a drive source, and is useful as the actuator that produces back-and-forth rotating vibration and that is used in, for example, an electric toothbrush.

What is claimed is:

1. An actuator comprising:
    a movable body that comprises:
        an outer yoke having opposing inner wall planes spaced a predetermined interval apart; and
        a magnet which is provided in the outer yoke and in which different magnetic pole planes oppose the opposing inner wall planes through air gaps;
    an output shaft provided in the movable body;
    a fixed body that comprises a coil which is located in the air gaps and which encircles the magnetic body;
    an elastic support part that movably supports the movable body in the fixed body; and
    an alternating current supplying section that supplies to the coil an alternating current of a frequency substantially equal to a resonance frequency of the movable body, wherein
    the movable body is supported through the elastic support part by the fixed body at an end orthogonal to an inner wall plane of the movable body, and
    the movable body moves in a twisting direction of the magnetic body and the output shaft during actuation of the actuator.

2. The actuator according to claim 1, wherein the magnet is provided in the outer yoke through a non-magnetic body.

3. The actuator according to claim 1, wherein the movable body is axially supported in the fixed body such that the movable body is rotatable around the output shaft.

4. The actuator according to claim 1, wherein the elastic support part comprises a viscoelastic body that is interposed between the fixed body and the movable body and that is deformable between the fixed body and the movable body.

5. An electric toothbrush comprising:
    an actuator according to claim 1; and
    a toothbrush part that is coupled to an output shaft of the actuator on the same shaft center as the output shaft and that comprises in a head part a hair bundle part provided orthogonal to an axial direction.

* * * * *